(12) United States Patent
Gold et al.

(10) Patent No.: US 7,413,904 B2
(45) Date of Patent: *Aug. 19, 2008

(54) HUMAN EMBRYONIC STEM CELLS HAVING GENETIC MODIFICATIONS

(75) Inventors: Joseph D. Gold, San Francisco, CA (US); Melissa K. Carpenter, London (CA); Margaret S. Inokuma, San Jose, CA (US); Chunhui Xu, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 10/948,956

(22) Filed: Sep. 24, 2004

(65) Prior Publication Data

US 2005/0164385 A1    Jul. 28, 2005

Related U.S. Application Data

(63) Continuation-in-part of application No. 10/235,094, filed on Sep. 4, 2002, said application No. 10/948,956 is a continuation-in-part of application No. 09/849,022, filed on May 4, 2001, now abandoned, and a continuation-in-part of application No. 09/530,346, filed as application No. PCT/US98/22619 on Aug. 29, 2000, now Pat. No. 6,800,480.

(60) Provisional application No. 60/220,064, filed on Jul. 21, 2000, provisional application No. 60/216,387, filed on Jul. 7, 2000, provisional application No. 60/213,739, filed on Jun. 22, 2000, provisional application No. 60/213,740, filed on Jun. 22, 2000, provisional application No. 60/175,581, filed on Jan. 11, 2000.

(51) Int. Cl.
*C12N 5/00* (2006.01)
*C12N 5/02* (2006.01)
*C12N 5/08* (2006.01)
*C12N 15/00* (2006.01)

(52) U.S. Cl. .................. 435/455; 435/366; 435/383

(58) Field of Classification Search ................ 435/325, 435/366, 383, 455; 424/93.2, 93.21
See application file for complete search history.

(56) References Cited

U.S. PATENT DOCUMENTS

| 5,464,764 | A | * | 11/1995 | Capecchi et al. ............... 435/6 |
| 5,523,226 | A | | 6/1996 | Wheeler |
| 5,591,625 | A | | 1/1997 | Gerson et al. |
| 5,843,780 | A | * | 12/1998 | Thomson ..................... 435/363 |
| 5,942,435 | A | | 8/1999 | Wheeler |
| 6,200,806 | B1 | | 3/2001 | Thomson |
| 6,800,480 | B1 | | 10/2004 | Bodnar et al. |
| 2005/0148070 | A1 | | 7/2005 | Thomson et al. |

FOREIGN PATENT DOCUMENTS

| EP | 0 695 351 B1 | 12/1999 |
| WO | WO 01/51616 A2 | 7/2001 |

OTHER PUBLICATIONS

Thomson et al. PNAS, 92:7844-7848, 1995).*
Lim et al. Proteomics 2002, 2, 1187-1203.*
Sambrook et al. Molecular Cloning, Book 3, 1989.*
Gao et al. Biochimica et Biophysica Acta, 1350: 1-5, 1997.*
Amsterdam et al. Gene, 173: 99-103, 1996.*
Eiges R et al, Establishment of Human Embryonic Stem Cell-Transfected Clones Carrying a Marker for Undifferentiated Cells, Curr Biol 11:514 (2001).
Gropp M et al, Stable Genetic Modification of Human Embryonic Stem Cells by Lentiviral Vectors, Mol Ther 7(2):281 (2003).
Ma Y et al, High-Level Sustained Transgene Expression in Human Embryonic Stem Cells Using Lentiviral Vectors, Stem Cells 21:111 (2003).
Schuldiner M et al, Selective Ablation of Human Embryonic Stem Cells Expressing a "Suicide" Gene, Stem Cells 21:257 (2003).
Zwaka TP et al, Homologous Recombination in Human Embryonic Stem Cells, Nat Biotech, 21:319 (2003).
Amit , M. et al., "Feeder layer-and serum-free culture of human embryonic stem cells,", *Biol. Reprod.* 70:837-45 (2004).
Baribault, H. & Kemler, R., "Embryonic stem cell culture and gene targeting in transgenic mice," *Mol. Biol. Med.* 6:481-92 (1989).
Berger, C. & Sturm, K., "Self renewal of embryonic stem cells in the absence of feeder cells and exogenous leukaemia inhibitory factor," *Growth Factors* 14:145-59 (1997).
Bradley, A., "Modifying the mouse: design and desire," *Biotechnol.* 10:534-9 (1992).
Lebkowski, J. et al., "Human embryonic stem cells: Culture, differentiation, and genetic modification for regenerative medicine applications," *Cancer J.* 7(Suppl. 2):S83-S94 (2001).
Pedersen, R. "Embryonic stem cells for medicine," *Sci. Amer.*, pp. 39-73 (Apr. 1999).
Rosler, E. et al., "Long-term culture of human embryonic stem cells in feeder-free conditions," *Dev. Dyn.* 229:259-74 (2004).
Smith, A. & Hooper, M., "Buffalo rat liver cells produce a diffusable activity which inhibits the diiferentation of murine embroyonal carcinoma and embryonic stem cells," *Dev. Biol.* 121:1-9 (1987).
Smith, A. et al., "Inhibition of pluripotential embryonic stem cell differentation by purified polypeptides," *Nature* 336:688-90 (1988).
Thomson, J. et al., "Embryonic stem cell lines derived from human blastocysts," *Science* 282:1145-7 (1998).
Xu, C. et al., "Feeder-free growth of undifferentiated human embryonic stem cells," *Nature Biotech.* 19:971-4 (2001).

* cited by examiner

*Primary Examiner*—Thaian N Ton
(74) *Attorney, Agent, or Firm*—E. Stewart Mittler (57) ABSTRACT

This disclosure provides a system for obtaining genetically altered primate pluripotent stem (pPS) cells. The role of the feeder cells is replaced by supporting the culture on an extracellular matrix, and culturing the cells in a conditioned medium. The cells can be genetically altered with a viral vector or DNA/lipid complex, and then selected for successful transfection by drug-resistant phenotype in the transfected cells. The system allows for bulk proliferation of genetically altered pPS cells as important products for use in human therapy or drug screening.

4 Claims, 5 Drawing Sheets

HUMAN EMBRYONIC STEM CELLS HAVING GENETIC MODIFICATIONS

REFERENCE TO RELATED APPLICATIONS

This application is a continuation-in-part of U.S. Ser. No. 09/849,022 (091/005), filed May 4, 2001 now abandoned, through which it claims priority to U.S. Ser. No. 60/175,581, filed Jan. 11, 2000; U.S. Ser. No. 60/213,740, filed Jun. 22, 2000: U.S. Ser. No. 60/213,739, filed Jun. 22, 2000; U.S. Ser. No. 60/216,387, filed Jul. 7, 2000; and U.S. Ser. No. 60/220,064, filed Jul. 21, 2000. This application is also a continuation-in-part of U.S. Ser. No. 10/235,094 (091/030), filed Sep. 4, 2002 (pending); and a continuation-in-part of 09/530,346 (061/005), filed Aug. 29, 2000 (now U.S. Pat. No. 6,800,480); which is the U.S. National Stage of PCT/US98/22619 (061/234PCT), filed Oct. 23, 1998, designating the U.S. and published as WO 99/20741 on Apr. 29, 1999; which claims priority to U.S. Ser. No. 08/990,560, filed Dec. 15, 1997 (abandoned); U.S. Ser. No. 08/956,684, filed Oct. 23, 1997 (abandoned); U.S. Ser. No. 08/961,628, filed Oct. 31, 1997 (abandoned); and 08/961,629, filed Oct. 31, 1997 (abandoned).

BACKGROUND

Recent discoveries have raised expectations that stem cells may be a source of replacement cells and tissues that are damaged in the course of disease, infection, or because of congenital abnormalities. Various types of putative stem cells differentiate when they divide, maturing into cells that can carry out the unique functions of particular tissues, such as the heart, the liver, or the brain. A particularly important discovery has been the development of pluripotent stem cells, which are thought to have the potential to differentiate into almost any cell type.

Early work on pluripotent stem cells was done in mice (reviewed in Robertson, Meth. Cell Biol. 75:173, 1997; and Pedersen, Reprod. Fertil. Dev. 6:543, 1994). Mouse stem cells can be isolated from both early embryonic cells and germinal tissue. Desirable characteristics of pluripotent stem cells are that they be capable of indefinite proliferation in vitro in an undifferentiated state, retain a normal karyotype, and retain the potential to differentiate to derivatives of all three embryonic germ layers (endoderm, mesoderm, and ectoderm). Mouse ES cells can be kept in the undifferentiated cells simply by having leukemia inhibitory factor (LIF) in the medium (Williams et al., Nature. 15:684, 1988). Thus, they can be genetically altered and drug selected in culture systems not containing feeder cells.

The development of preparations of human pluripotent stem cells has involved overcoming a number of technical difficulties, which makes them more challenging to grow and manipulate than mouse cells.

Thomson et al. (U.S. Pat. No. 5,843,780; Proc. Natl. Acad. Sci. USA 92:7844, 1995) were the first to successfully isolate and propagate pluripotent stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shambloff et al., Proc. Natl. Acad. Sci. USA 95:13726, 1998; and U.S. Pat. No. 6,090,622). Both hES and hEG cells are capable of long-term proliferation in vitro without differentiating, they have a normal karyotype, and they remain capable of producing a number of different cell types. Because of this, they hold considerable promise for use in human therapy, acting as a reservoir for regeneration of almost any tissue compromised by genetic abnormality, trauma, or a disease condition.

Thomson et al. teach that human ES cells require culturing on feeder cells in order to prevent them from differentiating. This represents a significant challenge to the usual methods of making genetically altered cells.

SUMMARY OF THE INVENTION

This disclosure provides an improved system for culturing primate pluripotent stem (pPS) cells in the absence of feeder cells. The role of the feeder cells is replaced by supporting the culture on an extracellular matrix, and culturing the cells in a suitable nutrient medium. Methods have been developed to genetically alter pPS cells by introducing the cells with a viral vector or DNA/lipid complex. The system described in this disclosure allows for bulk proliferation of genetically altered pPS cells and their derivatives for the production of important products for use in human therapy.

In one embodiment, the genetically altered pPS cells of this invention are made providing a composition of pPS cells essentially free of feeder cells; and transferring a polynucleotide into pPS cells in the composition. The pPS cells may be cultured in an environment comprising extracellular matrix components and a conditioned medium produced by collecting medium from a culture of feeder cells. After transfection, the cells can be preferentially selected for those that have been genetically altered with the polynucleotide. The polynucleotide may comprise a protein encoding region operably linked to a promoter that promotes transcription of the encoding region in an undifferentiated pPS cell. Exemplary polynucleotides are an adenoviral vector, a retroviral vector, or a DNA plasmid complexed with positively charged lipid. Exemplary pPS cells are human embryonic stem (hES) cells.

Other embodiments of the invention relate to the use of genetically altered pPS cells for drug screening or preparing cellular compositions for purposes of regenerative medicine.

These and other aspects of the invention will be apparent from the description that follows.

DETAILED DESCRIPTION

This disclosure provides a system for producing genetically altered primate pluripotent stem (pPS) cells, and differentiated precursor and mature cells that inherit the genetic alteration.

Embryonic stem cells are traditionally cultured on a layer of primary embryonic fibroblasts (Thomson, U.S. Pat. No. 5,843,780). The feeder cells provide important factors that allow the stem cells to proliferate without differentiation. This creates a complication for obtaining stem cells with genetic alterations, since successfully transfected cells cannot be selected by the standard technique of antibiotic resistance. The antibiotic will kill not only untransfected stem cells in the culture, but also the underlying feeder cell layer—leading to uncontrolled differentiation of the transfected stem cells.

It has been discovered that pPS cells can be genetically altered by setting them up in a culture system that is essentially free of feeder cells. Features in the culture system replace the role of feeder cells in promoting proliferation without differentiation. The culture environment is supported by a suitable substrate on the culture surface, such as extracellular matrix like Matrigel® or laminin. The culture system also contains medium with factors that effectively inhibit differentiation. In an exemplary preparation, undifferentiated hES colonies were harvested from hES cultures on feeders, and then seeded onto a Matrigel® substrate in medium conditioned by previously culturing with embryonic fibroblasts. The day after seeding, undifferentiated hES cells were visible as small colonies of about 100-2,000 cells, with a doubling rate of the order of 20-40 hours, which is comparable to hES grown on feeder cells.

pPS cells set up in feeder-free culture can be transfected with a suitable gene vector containing an antibiotic resistance gene, and then selected by including the antibiotic in the culture medium. The feeder-free system provides high levels of gene expression, and of transfection efficiency. In model experiments, ~15% of cells in feeder-free culture have been transfected with a marker gene, whereas the transfection efficiency on primary feeder layers is typically only 5% of undifferentiated hES cells transfected on primary feeder layers were positive, indicating that transfection efficiency is significantly enhanced using feeder-free culture conditions.

The techniques provided in this invention represent an important advance in the potential use of genetically altered pluripotent stem cells and their derivatives for research and therapeutic use. Further advantages of the invention will be understood from the sections that follow.

DEFINITIONS

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture.

Included in the definition of pPS cells are embryonic cells of various types, exemplified by human embryonic stem (hES) cells, defined below; embryonic stem cells from other primates, such as Rhesus or marmoset stem cells (Thomson et al., Proc. Natl. Acad. Sci. USA 92:7844, 1995; Developmental Biology 38:133, 1998); and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. It is beneficial to use pPS cells that are karyotypically normal and not derived from a malignant source.

Prototype "human Embryonic Stem cells" (hES cells) are described by Thomson et al. (Science 282:1145,1998; U.S. Pat. No. 6,200,806). The scope of the term covers pluripotent stem cells that are derived from a human embryo at the blastocyst stage, or before substantial differentiation of the cells into the three germ layers. Those skilled in the art will appreciate that except where explicitly required otherwise, the term includes primary tissue and established lines that bear phenotypic characteristics of hES cells, and derivatives of such lines that still have the capacity of producing progeny of each of the three germ layers.

pPS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells, and may contain at least 40%, 60%, or 80% in order of increasing preference (in terms percentage of cells with the same genotype that are undifferentiated).

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of pPS cells. A feeder free culture will contain less than about -5% feeder cells. Compositions containing less than 1%, 0.2%, 0.05%, or 0.01% feeder cells (expressed as % of total cells in the culture) are increasingly more preferred.

A "growth environment" is an environment in which cells of interest will proliferate in vitro. Features of the environment include the medium in which the cells are cultured, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, serum or serum replacement, and other exogenously added factors.

A "conditioned medium" is prepared by culturing a first population of cells in a medium, and then harvesting the medium. The conditioned medium (along with anything secreted into the medium by the cells) may then be used to support the growth of a second population of cells. Where a particular ingredient or factor is described as having been added to the medium, what is meant is that the factor (or a cell or particle engineered to secrete the factor) has been mixed into the medium by deliberate manipulation.

A "fresh medium" is a medium that has not been purposely conditioned by culturing with a different cell type before being used with the cell type it is ultimately designed to support. Otherwise, no limitations are intended as to its manner of preparation, storage, or use. It is added fresh (by exchange or infusion) into the ultimate culture, where it may be consumed or otherwise processed by the cell types that are present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. Also included are genetic alterations by any means that result in functionally altering or abolishing the action of an endogenous gene.

The genetic alteration is said to be "inheritable" if progeny of the altered cell has the same alteration. Determination of whether the genetic alteration is inheritable can be made by detecting presence of the polynucleotide template (e.g., by PCR amplification), or by detecting a phenotypic feature (such as expression of a gene product or effect thereof) that depends on the genetic alteration to be manifest.

The genetic alteration is said to be "stable" if it is inheritable through at least 4 rounds of cell replication, detectable as the presence of the polynucleotide template in a $7^{th}$ generation cell. Expression of a phenotype (at the mRNA, protein, or functional level) is said to be "stable" if the phenotypic feature in the $7^{th}$ generation cell is at least 10% (and often at least 50%) of that in the parental genetically altered cell. Stable expression indicates that the genetic alteration is also stable. The genetic alteration is said to be "ransient" if the polynucleotide template is absent from progeny of the original genetically altered cell by the $7^{th}$ cell division. Expression of a phenotype is said to be "transient" if the phenotypic feature in the $7^{th}$ generation cell is no more than 5% of that in the original genetically altered cell, whether due to loss of the template or because of some mechanism inhibiting expression of the template.

A "cell line" is a population of cells that can be propagated in culture through at least 10 passages. The population can be phenotypically homogeneous, or the population can be a mixture of measurably different phenotypes. Characteristics of the cell line are those characteristics of the population as a whole that are essentially unaltered after 10 passages.

A cell is described as "telomerized" if it has been genetically altered with a nucleic acid encoding a telomerase reverse transcriptase (TERT) of any species in such a manner that the TERT is transcribed and translated in the cell. The term also applies to progeny of the originally altered cell that have inherited the ability to express the TERT encoding region at an elevated level.

A cell line is described as "immortalized" if it has at least one of the following properties: 1) it has been genetically altered for elevated expression of telomerase reverse transcriptase (TERT), detectable, for example, as increased telomerase activity in TRAP assay; 2) for cell lines otherwise capable of no more than 15 population doublings, it has been genetically altered to extend its replicative capacity under suitable culture conditions to at least 20 population doublings; or 3) for cell lines otherwise capable of more than 15 population doublings, it has been genetically altered to significantly extend the replicative capacity of the cell line under typical culture conditions. This definition includes not only the original genetically altered cells, but also all progeny of such cells that meet these criteria.

General Techniques

For further elaboration of general techniques useful in the practice of this invention, the practitioner can refer to standard textbooks and reviews in cell biology, tissue culture, and embryology. Included are *Teratocarcinomas and embryonic stem cells: A practical approach* (E. J. Robertson, ed., IRL Press Ltd. 1987); Guide to Techniques in Mouse Development (P. M. Wasserman et al., eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., al.,1993).

Differentiation of stem cells is reviewed in Robertson, Meth. Cell Biol. 75:173, 1997; and Pedersen, Reprod. Fertil. Dev. 10:31,1998.

Methods in molecular genetics and genetic engineering are described generally in the current editions of *Molecular Cloning: A Laboratory Manual*, (Sambrook et al.); *Oligonucleotide Synthesis* (M. J. Gait, ed.,); *Animal Cell Culture* (R. I. Freshney, ed.); *Gene Transfer Vectors for Mammalian Cells* (Miller & Calos, eds.); *Current Protocols in Molecular Biology and Short Protocols in Molecular Biology, 3rd Edition* (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

General techniques used in raising, purifying and modifying antibodies, and the design and execution of immunoassays including immunocytochemistry, the reader is referred to *Handbook of Experimental Immunology* (Weir & Blackwell, eds.); *Current Protocols in Immunology* (Coligan et al., eds.); and *Methods of Immunological Analysis* (Masseyeff et al., eds., Weinheim: VCH Verlags GmbH).

General techniques in cell culture and media collection are outlined in *Large Scale Mammalian Cell Culture* (Hu et al., Curr. Opin. Biotechnol. 8:148, 1997); *Serum-free Media* (K. Kitano, Biotechnology 17:73, 1991); *Large Scale Mammalian Cell Culture* (Curr. Opin. Biotechnol. 2:375,1991); and *Suspension Culture of Mammalian Cells* (Birch et al., Bioprocess Technol. 19:251, 1990). Other reading of interest includes *Understanding Media* (M. McLuhan, Mentor N.Y., 1964) and *The Medium is the Massage* (M. McLuhan & Q. Fiore, Bantam N.Y., 1967).

Sources of Pluripotent Stem Cells

Suitable source cells for culturing and differentiation according to this invention include established lines of pluripotent cells derived from tissue formed after gestation. Exemplary primary tissue sources are embryonic tissue (such as a blastocyst), or fetal tissue taken any time during gestation, typically but not necessarily before 10 weeks gestation. Non-limiting exemplars are established lines of primate embryonic stem (ES) cells, exemplified below; and embryonic germ (EG) cells, described in Shamblott et al., Proc. Natl. Acad. Sci. USA 95:13726, 1998; and U.S. Pat. No. 6,090,622. Also contemplated is use of the techniques of this disclosure during the initial establishment or stabilization of such cells, in which case the source cells would be primary pluripotent cells taken directly from the tissues listed.

Establishing Lines of Human Embryonic Stem (hES) Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399,2000. Equivalent cell types to hES cells include their pluripotent derivatives, such as primitive ectoderm-like (EPL) cells, as outlined in WO 01/51610 (Bresagen).

Materials for the preparation of hES cell lines according to traditional methods are as follows. Serum-containing ES medium is made with 80% DMEM (typically knockout DMEM), 20% defined fetal bovine serum (FBS), 1% non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement (Gibco #10828-028), 1% non-essential amino acids, 1 mM L-glutamine, and 0.1 mM β-mercaptoethanol. Just before use, human bFGF is added to a final concentration of 4-8 ng/mL.

Mouse embryonic fibroblasts (mEF) for use as feeder cells can be obtained from outbred CF1 mice (SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2-3 d), they are split 1:2 into new flasks.

Feeder cells are propagated in mEF medium, containing 90% DMEM (Gibco #11965-092), 10% FBS (Hyclone #30071-03), and 2 mM glutamine. mEFs are propagated in T150 flasks (Corning #430825), splitting the cells 1:2 every other day with trypsin, keeping the cells subconfluent. To prepare the feeder cell layer, cells are irradiated at a dose to inhibit proliferation but permit synthesis of important factors that support hES cells (~4000 rads gamma irradiation). Six-well culture plates (such as Falcon #304) are coated by incubation at 37° C. with 1 mL 0.5% gelatin per well overnight, and plated with 375,000 irradiated mEFs per well. Feeder cell layers are used 5 h to 4 days after plating. The medium is replaced with fresh hES medium just before seeding.

hES cells can be isolated from human blastocyst obtained from human in vivo preimplantation embryos, in vitro fertilized embryos, or one cell human embryos expanded to the blastocyst stage (Bongso et al., Hum Reprod 4: 706, 1989). Human embryos can be cultured to the blastocyst stage in G1.2 and G2.2 medium (Gardner et al., Fertil. Steril. 69:84, 1998). The zona pellucida is removed from blastocysts by brief exposure to pronase (Sigma). The inner cell masses are isolated by immunosurgery or by mechanical separation, and plated on mouse embryonic feeder layers, or in feeder free culture as described below.

After 9 to 15 days, inner cell mass-derived outgrowths are dissociated into clumps either by exposure to calcium and magnesium-free phosphate-buffered saline (PBS) with 1 mM EDTA, by exposure to dispase, collagenase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette.

Propagation of pPS Cells in the Absence of Feeder Cells

This invention allows pPS to be propagated in an undifferentiated state, even in the absence of feeder cells. Feeder-free pPS cell cultures can be obtained either by passaging cells grown on feeder into feeder-free conditions, or by first deriving the cells from blastocysts into a feeder-free environment.

In the absence of feeders, the pPS cells are cultured in an environment that supports proliferation without differentiation. Aspects of culture that can affect differentiation include the substrate upon which the cells are cultured, the medium in which they are cultured, and the manner in which they are split and passaged to new culture environments.

pPS cells may be supported in feeder-free culture on an extracellular matrix. The matrix can be deposited by preculturing and lysing a matrix-forming cell line (WO 99/20741), such as the STO mouse fibroblast line (ATCC Accession No. CRL-1503), or human placental fibroblasts. The matrix can also be coated directly into the culture vessel with isolated matrix components. Matrigel® is a soluble preparation from Engelbreth-Holm-Swarm tumor cells that gels at room temperature to form a reconstituted basement membrane. Other suitable extracellular matrix components may include laminin, fibronectin, proteoglycan, entactin, heparan sulfate, and so on, alone or in various combinations. Substrates that can be tested using the experimental procedures described herein include not only other extracellular matrix components, but also polyamines, and other commercially available coatings. This invention contemplates adding extracellular matrix to the fluid phase of a culture at the time of passaging the cells or as part of a regular feeding. This invention also contemplates extracellular matrix deposited into the culture by cells within the culture (such as pPS cells that have formed around the periphery of an undifferentiated colony).

The pluripotent cells are plated onto the substrate in a suitable distribution and in the presence of a medium that promotes cell survival, propagation, and retention of the desirable characteristics. These characteristics benefit from careful attention to the seeding distribution. One feature of the distribution is the plating density. It has been found that plating densities of at least ~15,000 cells $cm^{-2}$ (typically 90,000 $cm^{-2}$ to 170,000 $cm^{-2}$) promote survival and limit differentiation.

Another consideration is cell dispersion. In one method, enzymatic digestion is halted before cells become completely dispersed (say, ~5 min with collagenase IV). The plate is then scraped gently with a pipette, and the cells are triturated into clumps of adherent cells, about 10-2000 cells in size, which are then passaged into the new culture environment. Alternatively, primate PS cells can be passaged between feeder-free cultures as a finer cell suspension, providing that an appropriate enzyme and medium are chosen, and the plating density is sufficiently high. By way of illustration, confluent human embryonic stem cells cultured in the absence of feeders are removed from the plates by incubating with 0.05% (wt/vol) trypsin and 0.053 mM EDTA for 5-15 min at 37° C. The remaining cells in the plate are removed, triturated with the pipette until dispersed into single cells and small clusters, and then replated. In another illustration, the cells are harvested without enzymes before the plate reaches confluence. The cells are incubated ~5 min in 0.5 mM EDTA alone in PBS, washed from the culture vessel, and then replated without further dispersal.

pPS cells plated in the absence of fresh feeder cells benefit from being cultured in a nutrient medium. The medium will generally contain the usual components to enhance cell survival, including isotonic buffer, essential minerals, and either serum or a serum replacement of some kind. To inhibit differentiation, the medium is formulated to supply some of the elements provided by feeder cells or their equivalents.

The base nutrient medium used for conditioning can have any of several different formulae. Exemplary serum-containing ES medium is made with 80% DMEM (typically KO DMEM), 20% defined fetal bovine serum (FBS), 1% non-essential amino acids, 1 mM L-glutamine, and 0.1 mM β-mercaptoethanol. Serum-free ES medium is made with 80% KO DMEM, 20% serum replacement, 1% non-essential amino acids, 1 mM L-glutamine, and 0.1 mM β-mercaptoethanol. Not all serum replacements work; an effective serum replacement is Gibco #10828-028.

Other suitable base media are X-VIVO™ 10 expansion medium (Biowhittaker) and QBSFυ-60 (Quality Biological Inc.) (Example 8). See also WO 98/30679 (Life Technologies Inc.) and U.S. Pat. No. 5,405,772 (Amgen). The medium will typically contain a protein nutrient, in the form of serum (such as FBS), serum replacement, albumin, or essential and non-essential amino acids in an effective combination. It will also typically contain lipids, fatty acids, or cholesterol as artificial additives or the HDL or LDL extract of serum. Other beneficial factors that can be included are hormones like insulin or transferrin, nucleosides or nucleotides, pyruvate, and a reducing agent such as β-mercaptoethanol.

Medium Additives

The nutrient medium used for culturing the pPS cells comprises one or more factors that promote proliferation of the pPS cells without differentiation. As will be apparent from the following description, the supplementation can occur by preculturing the medium with cells that secrete such factors, by adding such factors to the medium artificially, or by both techniques in combination.

Conditioned medium can be prepared by culturing irradiated primary mouse embryonic fibroblasts (Example 1) or other cells (Example 4) at a density of ~5-6×$10^4$ $cm^{-2}$ in a serum free medium such as KO DMEM supplemented with 20% serum replacement and ~4-8 ng/mL basic fibroblast growth factor (bFGF). The culture supernatant is harvested after ~1 day at 37° C. The cells are cultured in the medium for sufficient time to allow adequate concentration of released factors that support pPS cell culture. Typically, medium conditioned by culturing for 24 hours at 37° C. contains a concentration of factors that support pPS cell culture for at least 24 hours. However, the culturing period can be adjusted upwards or downwards, determining empirically what constitutes an adequate period. Medium that has been conditioned for 1-2 days is typically used to support pPS cell culture for 1-2 days, and then exchanged.

Non-conditioned medium that supports pPS cell growth in an undifferentiated state can be created by adding to a suitable base medium certain factors that invoke the appropriate signal transduction pathways in undifferentiated cells. The fibroblast growth factor family is especially effective in this regard. Exemplary are basic FGF (FGF-2), and FGF-4, but other members of the family can also be used. Also suitable are species homologs, artificial analogs, antibodies to the respective FGF receptor, and other receptor activator molecules. It has been determined from gene expression analysis that undifferentiated hES cells express receptors for acidic FGF (FGF-1). At a sufficient concentration (40-80 ng/mL, depending on other conditions), FGF alone is sufficient to promote growth of hES cells in an undifferentiated state.

Additional factors can be identified that facilitate the action of FGF and equivalents in their support of undifferentiated pPS cell growth. The method involves combining a plurality of factors into functional groups, and culturing the cells with the groups in various combinations. Once the effective groups are determined, the rest can be eliminated, and the group can be dissected to determine the minimal effective combination.

As a supplement to FGF, ligands that bind c-kit, such as stem cell factor (SCF, Steel factor), antibodies to c-kit, and other activators of the same signal transduction pathway may also be beneficial. SCF is dimeric and occurs in soluble and membrane-bound forms. It transduces signals by ligand-mediated dimerization of c-kit, which is a receptor tyrosine kinase related to the receptors for platelet-derived growth factor (PDGF), macrophage colony-stimulating factor, Flt-3 ligand and vascular endothelial growth factor (VEGF). Also of interest are factors that elevate cyclic AMP levels, such as forskolin. These factors or their equivalents may be used individually or in an effective combination with other influential factors in the medium, as already described.

The formulations provided in the Example section below were primarily designed for culturing hES cells. Where appropriate, the illustrations in this disclosure can be adapted to other types of pPS cells and multipotent cells by accommodating the known properties of the cells. For example, the hEG cells claimed in U.S. Pat. No. 6,090,622 are dependent on the presence of both bFGF and an inducer of gp130 (such as LIF or Oncostatin-M). The culture media for growing hEG cells can be adapted accordingly.

Each of the conditions described here can be optimized independently, and certain combinations of conditions will prove effective upon further testing. Such optimization is a matter of routine experimentation, and does not depart from the spirit of the invention provided in this disclosure.

Characteristics of pPS Cells Grown in the Absence of Feeder Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique, and compared to published human karyotypes. It is desirable to obtain cells that have a "normal karyotype", which means that the cells are euploid, wherein all human chromosomes are present and are not noticeably altered.

Primate ES cells typically express the stage-specific embryonic antigens (SSEA) 3 and 4, and markers detectable using antibodies designated Tra-1-60 and Tra-1-81. Undifferentiated hES cells also typically express the transcription factor Oct-3/4, Cripto, gastrin-releasing peptide (GRP) receptor, podocalyxin-like protein (PODXL), and human telomerase reverse transcriptase (hTERT) (US 2003/0224411 A1), as detected by RT-PCR.

Creating Immortalized Cell Lines

Where it is desirable to increase the replicative capacity of feeder cells or other cell types, they can be telomerized by genetically altering them with a suitable vector so that they express the telomerase catalytic component (TERT). Particularly suitable is the catalytic component of human telomerase (hTERT), provided in International Patent Publication WO 98/14592. For some applications, other TERT sequences can be used (mouse TERT is provided in WO 99/27113).

Typically, the vector will comprise a TERT encoding region under control of a heterologous promoter that will promote transcription in the intended undifferentiated or differentiated cell line. Sequences that can drive expression of the TERT coding region include viral LTRs, enhancers, and promoters (such as MPSV, SV40, MoLV, CMV, MSCV, HSV TK), eukaryotic promoters (such as β-actin, ubiquitin, EF1α, and PGK) or combinations thereof (for example, the CMV enhancer combined with the β-actin promoter). Expression of a marker gene can be driven by the same promoter as the TERT gene, either as a separate expression cassette, as part of a polycistronic transcript (in which the coding regions of TERT and the marker gene are separated by an IRES sequence, allowing both individual proteins to be made from a single transcript driven by a single promoter), or as part of the same cassette (a fusion between the coding regions of both TERT and the marker gene, producing a protein that provides the functions of both TERT and the marker gene). Transfection and expression of telomerase in human cells is described in Bodnar et al., Science 279:349, 1998 and Jiang et al., Nat. Genet. 21:111, 1999.

Before and after telomerization, telomerase activity and hTERT expression can be determined using standard reagents and methods. For example, pPS cells are evaluated for telomerase using TRAP assay (Kim et al., Science 266:2011, 1997; Weinrich et al., Nature Genetics 17:498, 1997). The following assay kits are available commercially for research purposes: TRAPeze® XK Telomerase Detection Kit (Cat. s7707; Intergen Co., Purchase N.Y.); and TeloTAGGG Telomerase PCR ELISAplus (Cat. 2,013,89; Roche Diagnostics, Indianapolis Ind.). hTERT expression can also be evaluated at the mRNA by RT-PCR. The following assay kit is available commercially for research purposes: LightCycler TeloTAGGG hTERT quantification kit (Cat. 3,012,344; Roche Diagnostics).

Other methods of immortalizing cells are also contemplated, such as genetically altering the cells with DNA encoding the SV40 large T antigen (U.S. Pat. No. 5,869,243, International Patent Publication WO 97/32972), infecting with Epstein Bar Virus, introducing oncogenes such as myc and ras, introducing viral replication genes such as adenovirus E1a, and fusing cells having the desired phenotype with an immortalized cell line. Transfection with oncogenes or oncovirus products is usually less suitable when the cells are to be used for therapeutic purposes.

Telomerized Feeder Cells

It has been discovered that cells with particular characteristics differentiated from human embryo derived cells can be used to support culture of undifferentiated pPS cells. Primary mouse embryonic feeder cells support pPS cell culture, but later-stage fibroblasts may not. It turns out that mouse embryonic feeder cells transfected to express the hTERT gene retain their ability to support pPS cells. This permits the user to develop immortalized and genetically modified feeder cells that can be used in the course of genetic selection (Examples 4 and 5). Alternatively, feeder cells of human origin can be obtained by differentiating hES cells into a cell line (typically with features of fibroblasts or mesenchymal cells) that secretes the factors that support the undifferentiated cell phenotype (Example 4).

Genetic Alteration of Pluripotent Stem Cells

This disclosure provides an important new process for obtaining pPS cells that have been genetically altered. The genetic alteration may be transient, or stable and inheritable as the cells divide. The genetically altered cells can be maintained in undifferentiated pluripotent form in culture, or they can be differentiated into other types of cells still retaining the genetic alteration. Effective methods have been discovered that allow hES cells to be genetically altered when grown on primary feeder cells. Methods are also provided in which hES cells are plated in a feeder-free environment before transfection, which provides a number of important advantages.

The polynucleotide to be transferred in the cell typically provides a function that will change the phenotype of the cell or its progeny in a desirable fashion. For example, it may contain an encoding region under control of a promoter that promotes transcription in undifferentiated hES cells, or in differentiated cells of a particular lineage. It may also affect endogenous gene expression by a suitable mechanism, such as antisense reactivity, triplex formation, or ribozyme action.

Suitable methods for transferring vector plasmids into hES cells include lipid/DNA complexes, such as those described in U.S. Pat. Nos. 5,578,475; 5,627,175; 5,705,308; 5,744,335; 5,976,567; 6,020,202; and 6,051,429. Suitable reagents include lipofectamine, a 3:1 (w/w) liposome formulation of the poly-cationic lipid 2,3-dioleyloxy-N-[2(sperminecarboxamido)ethyl]-N,N-dimethyl-1-propanaminium trifluoroacetate (DOSPA) (Chemical Abstracts Registry name: N-[2-(2,5-bis[(3-aminopropyl)amino]-1-oxpentyl)amino] ethyl]-N,N-dimethyl-2,3-bis(9-octadecenyloxy)-1-propanaminium trifluoroacetate). Exemplary is the formulation Lipofectamine 2000™ (available from Gibco/Life Technologies # 11668019). Other reagents include: FuGENE™ 6 Transfection Reagent (a blend of lipids in non-liposomal form and other compounds in 80% ethanol, obtainable from Roche Diagnostics Corp. # 1814443); and LipoTAXI™ transfection reagent (a lipid formulation from Invitrogen Corp., # 204110).

Suitable viral vector systems for producing hES cells with stable genetic alterations are based on adenovirus and retrovirus, and may be prepared using commercially available virus components.

For many applications, genetic alteration of hES cells requires attention to two different agenda achieving sufficiently high efficiency of genetic alteration, and performing the alteration in a manner that does not promote differentiation of the hES cells along an undesired pathway. Screening of various transfection and transduction systems, and optimization of reaction timing and conditions, can be conveniently performed in experiments using an expression vector with an encoding region for a detectable label. Particularly convenient labels are intrinsically fluorescent, such as luciferase, or green fluorescent protein (GFP). The label may also be an enzyme that can be detected in histopathology or quantitated by enzyme reaction. Examples include alkaline phosphatase, and β-galactosidase. The label may also be a cell-surface protein that can be stained with labeled antibody and quantitated, for example, in a fluorescence activated cell counting device. Once an effective system has been identified and optimized, the encoding region for the label may then be substituted with the gene of interest.

To monitor genetically altered cells for differentiation, the cells can be tested for expression of markers characteristic of pPS cells, such as SSEA-4, OCT-4, and TERT. Transfection efficiencies can thereby be calculated as a percentage of cells bearing the undifferentiated phenotype. The pluripotency of genetically altered cells can also be confirmed by inducing differentiation, either in vitro (e.g., via embryoid body formation) or in vivo (by teratoma formation), and comparing the types of cells produced with those produced by hES cells not genetically altered.

By these criteria, and tracking transfection with a GFP containing plasmid vector and surface expression of SSEA-4, it has been determined that efficiency of genetic alteration can generally be improved by detaching pPS cells using collagenase, replating, and allowing the cells to stabilize for 48 h before adding the vector. High efficiency can also be achieved by detaching the cells with 0.5 mM EDTA, replating, and stabilizing for 24 h before adding the vector. Peak expression of markers such as GFP occur ~24 h later.

Efficiencies of genetic alteration are rarely 100%, and it is usually desirable to enrich the population for cells that have been successfully altered. When hES cultures on fibroblast feeder cells are used, then the efficiency may be 5 to 20% of the undifferentiated cells. The genetically altered cells can be enriched by taking advantage of a functional feature of the new genotype. For example, where the pPS cells are transfected with a label such as GFP, or with an immunostainable surface marker such as NCAM, then the pPS cells can be suspended, separated by fluorescence-activated cell sorting, and replated. The reader is cautioned that complete separation of pPS cells usually promotes differentiation.

A particularly effective way of enriching genetically altered cells is positive selection using resistance to a drug such as neomycin or puromycin. To accomplish this, the cells can be genetically altered by contacting simultaneously with vector systems for the marker gene or gene of interest, and a vector system that provides the drug resistance gene. If the proportion of drug resistance gene in the mixture is low (say, 3:1), then most drug resistant cells should also contain the gene of interest. Alternatively, the drug resistance gene can be built into the same vector as the gene of interest. After transfection has taken place, the cultures are treated with the corresponding drug, and untransfected cells are eliminated. Unfortunately, feeder cells in the hES culture would normally also be susceptible to the drug.

To overcome this problem, this disclosure also provides feeder cells that are drug resistant. Cells that are known to provide the environment suitable for propagating pPS cells without differentiation can be introduced with a drug resistance gene, and then reevaluated for their ability to act as feeder cells. Alternatively, feeder cells (such as primary mouse fibroblasts) can be made from non-human mammals that have been rendered transgenic for a drug resistance gene. Such mice are available commercially; e.g., from Jackson Laboratories. The feeder cells can also be immortalized by genetically altering with an expression system for telomerase reverse transcriptase (TERT), or the SV40 Large T Antigen.

Example 4 illustrates a permanent feeder cell line designated NHG190 that has drug resistance genes for hygromycin, neomycin, and puromycin, and which has been telomerized. Surprisingly, despite all the manipulations and genetic perturbations, the cells are still highly effective feeders, providing the matrix substrate and cofactors that support proliferation of hES cells without differentiation. NHG190 cells are also suitable for making conditioned medium that support hES cells in feeder-free culture. Example 5 illustrates how drug-resistant feeder cells can be used for long-term selection of hES cells genetically altered with a drug-resistant gene.

It has been discovered that pPS cells are especially amenable to genetic alteration when they are grown in feeder-free culture (illustrated in Example 6). Transient transfection using DNA/lipid complexes can be as high as 60%. The cells are easier to manipulate, and there are no feeder cells around to act as a sink for the vector. Drug selection does not require availability of a drug-resistant feeder cell. The number of undifferentiated pPS colonies that grow out after transfection may also be improved.

Following genetic alteration and drug selection (on drug-resistant feeders or feeder-free culture), it is possible to pick colonies that demonstrate the altered phenotype, and culture them separately. The picked colonies are dispersed into small clumps of 25-100 cells, and replated in a suitable environment. Using some or all of the strategies outlined in this section and elsewhere in the disclosure, it is possible to achieve cultures of pPS cells in which at least ~25%, 50%, 75%, or even 90% of the undifferentiated cells have been genetically altered.

Use of Genetically Modified Cells

This description provides a method by which large numbers of pluripotent cells can be genetically altered, and then differentiated into committed precursor cells or terminally differentiated cells.

This can be done in order to instill the pPS cells with a feature that is desirable in the undifferentiated state (e.g., by expression of a gene that helps maintain the undifferentiated cell phenotype. Alternatively, the genetic alteration may be imparted so that when the pPS cells are differentiated, the resulting tissues have a desirable property.

Drug Screening

Genetically modified pPS cells or their differentiated derivatives can be used to screen for factors (such as small molecule drugs, peptides, polynucleotides, and the like) or conditions (such as culture conditions or manipulation) that affect the characteristics of pPS cells in culture. This system has the advantage of not being complicated by a secondary effect caused by perturbation of the feeder cells by the test compound. In one application, growth affecting substances are tested. The medium is withdrawn from the culture and an alternative medium is substituted. Different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cells according to the test protocol, and then determining whether the treated cell develops functional or phenotypic characteristics of a differentiated cell of a particular lineage.

pPS cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. The screening may be done, for example, either because the compound is designed to have a pharmacological effect on certain cell types, or because a compound designed to have effects elsewhere may have unintended side effects.

Cytotoxicity can be determine by the effect on cell viability, survival, morphology, and the expression of certain markers and receptors. The reader is referred to A. Vickers (pp 375-410 in *In vitro Methods in Pharmaceutical Research*, Academic Press, 1997) for further elaboration. Effect of cell function can be assessed using any standard assay to observe phenotype or activity, such as marker expression, receptor binding, contractile activity, electrophysiology, or the ability to metabolize the test compound. For use of pPS derived hepatocytes for drug screening, the reader is referred to U.S. Pat. No. 6,506,574, and WO 01/81549.

Therapeutic Compositions pPS cells of this invention can be differentiated into cell types useful for tissue reconstitution or regeneration. The cells can be genetically altered in a manner that stabilizes the differentiated cell type intended for therapy, promotes engraftment, or prevents resumption of the undifferentiated phenotype in vivo.

U.S. Pat. No. 6,576,464 and United Kingdom Patent GB 2374076 B1 describe genetic alterations of hES cells with a construct that prevents reemergence of the undifferentiated cell phenotype after differentiation. The transfected gene comprises an encoding region that is lytic to the cell, or which causes clearance by way of a cell-surface determinant, expressed under control of a promoter that causes expression in the undifferentiated cell (such as Oct-3/4 or hTERT).

The hES cells can also be genetically altered to prevent or modify expression of a phenotype that could mediate immune rejection of its differentiated progeny: such as an a blood group antigen, or an allogeneic HLA antigen.

U.S. Patent Publications US 2002/019046 A1 and US 2003/0103949 A1 describe the differentiation of hES cells into neural cells, such as may be useful for treating Parkinson's disease. Publication US 2003/0036194 A1 describes differentiation of hES cells into mesenchymal cells and osteoblasts. Publication US 2003/0022367 A1 describes the making of cardiomyocytes. Publication US 2003/0153082 A1 describes differentiation of hES cells into hematopoietic cells of various types. Publication US 2003/0138948 A1 describes the making of islet cells from hES cells for the treatment of diabetes. Publication US 2003/0109038 A1 describes derivation of hES cells into chondrocytes. Publication US 2003/0109038 A1 describes the making of oligodendrocytes from hES cells for treatment of spinal cord injury. Depending on the conditions used, cell populations of hepatocytes, neural cells, and other cell types that are well over 50% homogeneous (as much as 75%, 90%, or 98% homogeneous) can be obtained Any of these cell types may contain genetic alterations made before or after differentiation. Making the modification at the undifferentiated stage provides the user with the advantage of establishing a reservoir of modified cells that can be expanded at will, and then differentiated into the therapeutic cell type when needed. With regards to the differentiation and use of the genetically modified pPS cells of this invention, and the description of particular genes that are useful to express in pPS derived cells, the disclosures listed in the preceding paragraph are hereby incorporated herein by reference.

Cells prepared according to this invention that are useful for human or veterinary therapy are optimally supplied in a pharmaceutical composition, comprising an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The compositions may be packaged with written instructions for use of the cells in tissue regeneration, or restoring a therapeutically important metabolic function.

The examples that follow are provided by way of further illustration, and are not meant to imply any limitation in the practice of the claimed invention.

EXAMPLES

Example 1

Growing hES Cells in the Absence of Feeder Cells

Undifferentiated hES cells isolated on primary mouse embryonic feeder cells were propagated in the absence of feeder cells. The culture wells were coated with Matrigel®, and the cells were cultured in the presence of conditioned nutrient medium obtained from a culture of irradiated primary fibroblasts.

Preparation of Conditioned Media (CM) From Primary Mouse Embryonic Fibroblasts (mEF):

Fibroblasts were harvested from T150 flasks by washing once with $Ca^{++}/Mg^{++}$ free PBS and incubating in 1.5-2 mL trypsin/EDTA (Gibco) for about 5 min. After the fibroblasts detached from the flask, they were collected in mEF media (DMEM+10% FBS). The cells were irradiated at 4000 rad (508 sec at 140 kV: shelf setting 6 in a Torrex generator), counted and seeded at about 55,000 cells $cm^{-2}$ in mEF media (525,000 cells/well of a 6 well plate). After at least 4 hours the media were exchanged with SR containing ES media, using 3-4 mL per 9.6 cm well of a 6 well plate. Conditioned media was collected daily for feeding of hES cultures. Alternatively, medium was prepared using mEF plated in culture flasks, exchanging medium daily at 0.3-0.4 mL $cm^{-2}$. Before addition to the hES cultures, the conditioned medium was supplemented with 4 ng/mL of human bFGF (Gibco). Fibroblasts cultures were used in this system for about 1 week, before replacing with newly prepared cells.

Matrigel® Coating:

Growth Factor Reduced Matrigel® or regular Matrigel® (Becton-Dickinson, Bedford Mass.) was thawed at 4° C. The Matrigel® was diluted 1:10 to 1:500 (typically 1:30) in cold KO DMEM. 0.75-1.0 mL was added to each 9.6 $cm^2$ well, and incubated at room temperature for 1 h, or at 4° C. at least overnight. The coated wells were washed once with cold KO DMEM before adding cells. Plates were used within 2 h after coating, or stored in DMEM at 4° C. and used within ~1 week.

Human ES Culture:

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 μL pipet tip under a microscope or by scraping and dissociating into small clusters in conditioned medium (CM). These cells were then seeded onto Matrigel® in conditioned media at 15 colonies to each 9.6 $cm^2$ well (if 1 colony is ~10,000 cells, then the plating density is ~15,000 cells $cm^{31} 2$).

The day after seeding on Matrigel®, hES cells were visible as small colonies (~100-2,000 cells) and there were cells in between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split by incubating with 1 mL ~200 U/mL Collagenase IV solution in KO DMEM for ~5 minutes at 37° C. The collagenase solution was aspirated, 2 mL hES medium was added per well, and the hES cells were scraped from the dish with a pipette. The cell suspension was transferred to a 15 mL conical tube, brought up to a volume of 6 mL, and gently triturated to dissociate the cells into small clusters of 10-2000 cells. The cells were then re-seeded on Matrigel® coated plates in CM, as above. Cells were seeded at a 1:3 or 1:6 ratio, approximately 90,000 to 170,000 cells $cm^{-2}$, making up the volume in each well to 3 mL. Medium was changed daily, and the cells were split and passaged again at 13 d and again at 19 d after initial seeding.

Undifferentiated hES cells express SSEA-4, Tra-1-60, Tra-1-81, OCT-4, and hTERT. In order to assess whether the cells maintained in feeder-free conditions retained these markers, cells were evaluated by immunostaining, reverse transcriptase PCR amplification, and assay for telomerase activity. As assayed by fluorescence-activated cell sorting, cells on Matrigel®, laminin, fibronectin or collagen IV expressed SSEA-4, Tra-1-60 and Tra-1-81. There-was-very little expression of SSEA-1, a glycolipid that is not expressed by undifferentiated hES cells. Immunocytochemistry analysis shows that SSEA-4, Tra-1-60, Tra-1 -81, and alkaline phosphatase were expressed by the hES colonies on Matrigel® or laminin, as seen for the cells on feeders—but not by the differentiated cells in between the colonies.

Figure 1:
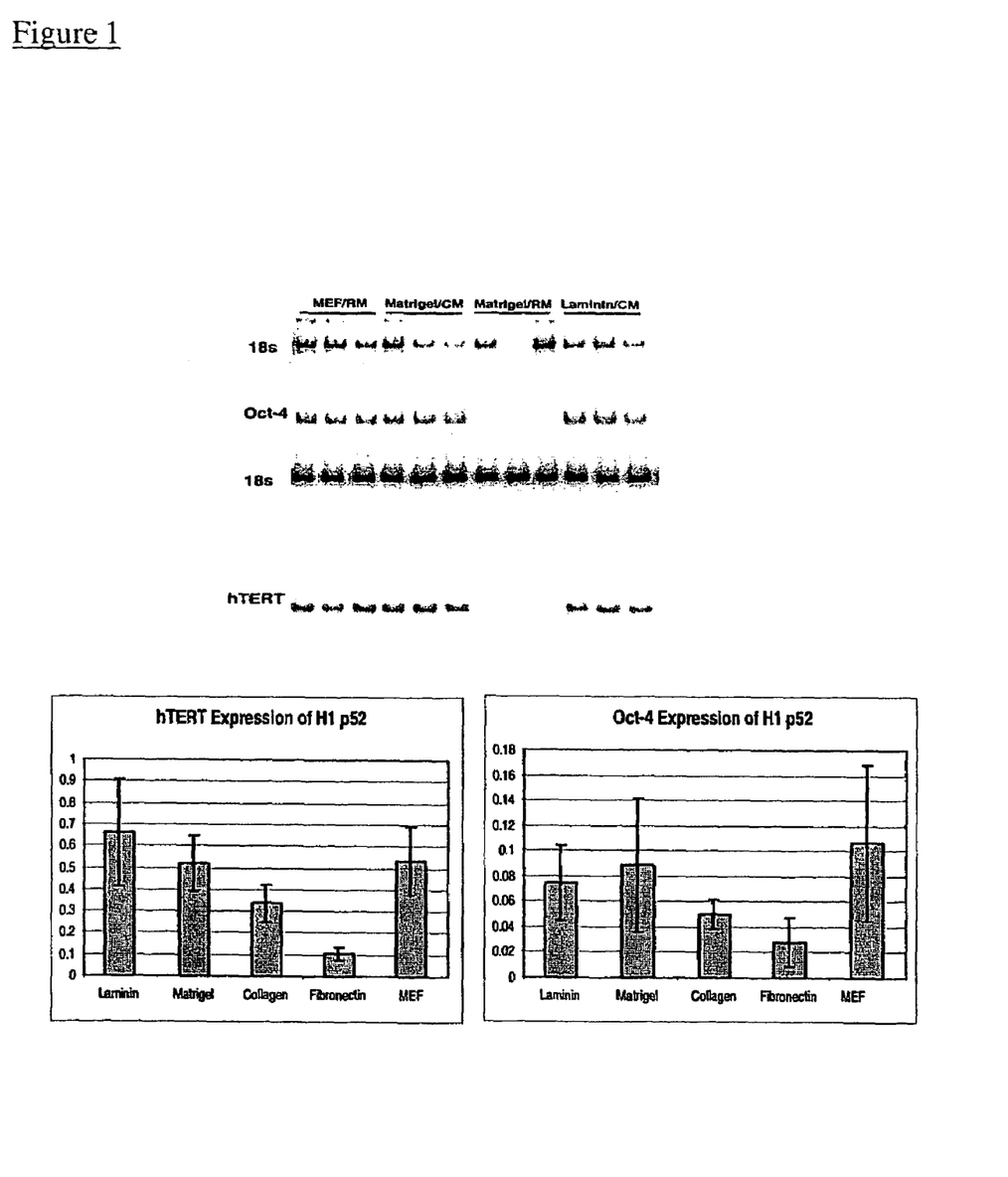
FIG. 1 provides an analysis of OCT-3/4 and hTERT expression in hES cells cultured with feeder cells (mEF) or extracellular matrix (Matrigel®) or laminin) with regular medium (RM) or conditioned medium (CM). The upper panel is a copy of a gel showing OCT-4 and hTERT expression at the mRNA level by RT-PCR. The lower panel is a bar graph comparing the level of expression for cells grown on different substrates, expressed as the ratio of OCT-4 or hTERT to the 18s standard. hES cells grown on Laminin and Matrigel® in conditioned medium have similar expression patterns to those of cells grown on a feeder layer.
Figure 2:
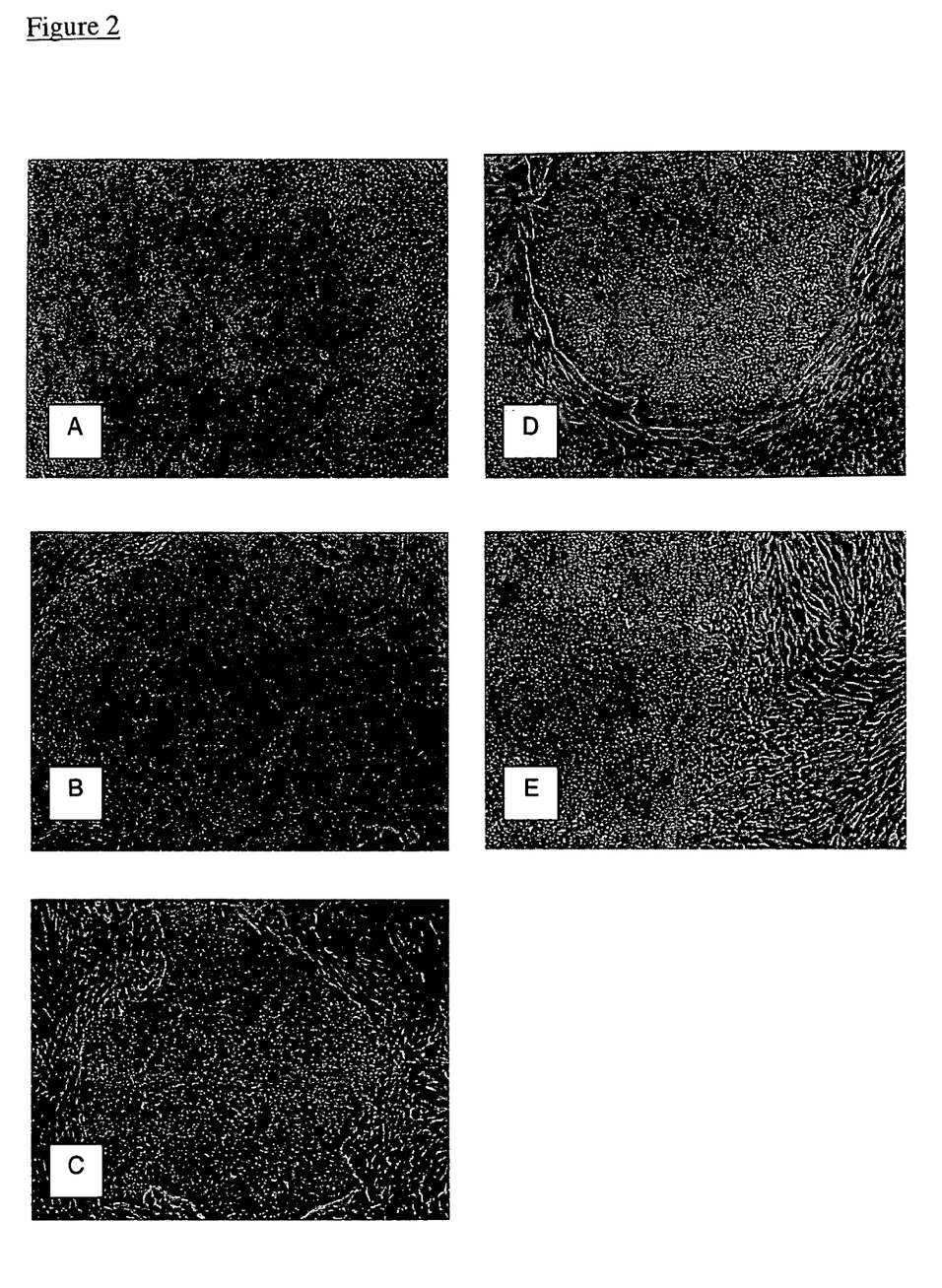
FIG. 2 shows colonies of hES cell at the end of 6 passages (sufficient for full adaptation) in various media formulations. (A) mEF conditioned medium+bFGF (8 ng/mL); (B) X-VIVO™ 10+bFGF (40 ng/mL); (C) X-VIVO™ 10+bFGF (40 ng/mL) +stem cell factor (SCF, Steel factor) (15 ng/mL); (D) X-VIVO™ 10+bFGF (40 ng/mL)+Flt3 ligand (75 ng/mL); (E) QBSF™-60+bFGF (40 ng/mL).

FIG. 1 shows OCT-1 and hTERT expression of Hi cells on feeders and off feeders, as detected by reverse-transcriptase PCR amplification. For radioactive relative quantification of individual gene products, QuantumRNA™ Alternate18S Internal Standard primers (Ambion, Austin Tex., USA) were employed according to the manufacturers instructions. Briefly, the linear range of amplification of a particular primer pair was determined, then coamplified with the appropriate mixture of alternate 18S primers:competimers to yield PCR products with coinciding linear ranges. Before addition of AmpliTaq™ (Roche) to PCR reactions, the enzyme was pre-incubated with the TaqStart™ antibody (ProMega) according to manufacturers instructions. Radioactive PCR reactions were analyzed on 5% non-denaturing polyacrylamide gels, dried, and exposed to phosphoimage screens (Molecular Dynamics) for 1 hour. Screens were scanned with a Molecular Dynamics Storm 860 and band intensities were quantified using ImageQuant™ software. Results are expressed as the ratio of radioactivity incorporated into the hTERT or OCT-4 band, standardized to the radioactivity incorporated into the 18s band.

The transcription factor OCT-4 is normally expressed in the undifferentiated hES cells and is down-regulated upon differentiation. The cells maintained on Matrigel® or laminin in conditioned medium (CM) for 21 days express OCT-4, whereas cells maintained in Matrigel® in unconditioned regular medium (RM) did not. Cells maintained on fibronectin or collagen IV, which showed a large degree of differentiation, expressed lower levels of OCT-4 compared to cells on feeders, Matrigel® or laminin.

Telomerase activity was measured by TRAP assay (Kim et al., Science 266:2011, 1997; Weinrich et al., Nature Genetics 17:498, 1997). All the cultures conditions showed positive telomerase activity after 40 days on Matrigel®, laminin, fibronectin or collagen IV in mEF conditioned medium.

Example 2

Growing hES Cells in Fresh Medium

Subsequent experiments investigated how different growth factors influence the proliferation and maintenance of undifferentiated hES cells using medium that had not previously been conditioned.

hES cells passaged 20 times in conditioned medium were weaned onto an alternative medium designed for proliferation of human hematopoietic cells. X-VIVO™ 10 expansion medium was obtained from Biowhittaker; QBSF™-60 was obtained from Quality Biological Inc. The X-VIVO™ 10 formulation contains pharmaceutical grade human albumin, recombinant human insulin and pasteurized human transferrin. Exogenous growth factors, artificial stimulators of cellular proliferation or undefined supplements are not included in the X-VIVO™ 10 medium. They are also devoid of any protein-kinase C stimulators. QBSF™-60 is a serum-free formulation that contains recombinant or pasteurized human proteins. For use in these experiments, the X-VIVO™ 10 medium was supplemented with 2 mM L-glutamine, 1% non-essential amino acids (Gibco), 0.1 mM β-mercaptoethanol, and 8 ng/mL bFGF. The medium was further supplemented with 8 ng/mL or 40 ng/mL of bFGF (Gibco); 40 ng/mL of bFGF and 15 ng/mL of SCF (R & D System); or 40 ng/mL of bFGF and 75 ng/mL of Flt3 ligand (R & D System). QBSF™-60 medium was supplemented with 0.1 mM β-mercaptoethanol, 1% non-essential amino acids (Gibco) and 40 ng/mL of bFGF. hES cells cultured in mEF conditioned medium was used as control in these experiments.

The hES cells were first passaged onto Matrigel® coated plates using collagenase IV, and cultured for 2 days with conditioned medium. On day 2, the conditioned medium was replaced with 80% unconditioned ES medium plus 20% expansion medium. Cells were fed fresh daily and passaged weekly. The proportion of expansion medium was increased by 20% approximately every 2 days until the cells were completely weaned, and then grown until they had been passaged 6 more times.

The following table shows the average total cell expansion per passage, for undifferentiated hES cells cultured for 4 passages in mEF conditioned medium, or for 7 passages in X-VIVO™ 10 or QBSFT™-60.

TABLE 1

Growth Rates for ES Cell Cultures

| Medium | Average Cell Expansion per Passage |
|---|---|
| mEF conditioned medium | 2.2 fold |
| X-VIVO ™ 10 + bFGF (40 ng/mL) | 6.0 fold |
| X-VIVO ™ 10 + bFGF (40 ng/mL) + SCF (15 ng/mL) | 8.2 fold |
| X-VIVO ™ 10 + bFGF (40 ng/mL) + Flt3 ligand (75 ng/mL) | 5.0 fold |
| QBSF ™-60 + bFGF (40 ng/mL) | 6.4 fold |

RNA was isolated from the cells using High Pure RNA Isolation Kit (Roche Diagnostics) and evaluated by Taqman™ assay (real time RT-PCR). The gene expression in each of the test condition was compared with expression in the culture in conditioned medium. The analysis showed expression of hTERT and Oct-3/4 decreased somewhat upon adaptation to unconditioned X-VIVO™ 10 or QBSF™-60 medium (first four bars in each set), but returned to standard levels when the cells were passaged back into mEF conditioned medium.

To confirm that cells cultured in unconditioned medium retain their pluripotency, embryoid bodies were formed and analyzed by immunocytochemistry for phenotypic markers representing each of the three germ layers. After passage 7 in expansion medium, the cells were dissociated into small clumps using 200 U/mL collagenase IV at 37° C. for 10 min, placed in suspension culture in differentiation medium (DMEM+10% FBS) for 4 days, then transferred onto poly-L-ornithine hydrobromide coated plates for a further 10 days. They were fixed in 4% paraformaldehyde, permeabilized, and labeled by immunocytochemistry. hES cells passaged 7 times in unconditioned X-VIVO™ 10 medium stained for α-fetoprotein (representing endoderm); muscle actin (representing mesoderm), and β-tubulin III (representing ectoderm).

Example 3

Genetic Alteration of hES Cells on mEF Feeder Layer

This example provides conditions for introducing genetic alterations into hES cells grown on primary mEFs as already described. Before transfecting, hES cells were removed from the feeder layer with collagenase (~200 units/mL), suspended in a final volume of 18 mL, and plated at 3 mL/well in 6 well plates pre-coated with gelatin and primary mEF feeder cells.

The replated cells were then tested with different transfection systems, including: Mammalian Transfection Kit (CaPO4 and DEAE reagents), Stratagene cat # 200285; TransIT-LT1 Mirus (Panvera), cat # MIR 2310; Polybrene (Sigma); Poly-L-Lysine (Sigma); Superfect™ (Qiagen); Effectene™ (Qiagen); Lipofectin™ (Life Technologies); Lipofectamine (differs from Lipofectamine 2000™) (Life Technologies); Cellfectin™ (Life Technologies); DMRIE-C (Life Technologies); Lipofectamine 2000 (Life Technologies); and electroporation using BioRad™ Gene pulser.

Under the conditions used, Lipofectamine 2000™ (Gibco Life Technologies cat # 11668019, patent pending) and FuGENE™ (trademark of Fugent L.L.C.; a proprietary blend of lipids and other components, purchased from Roche Diagnostic Corporation cat # 1 814 443) both resulted in good transfection efficiency. The efficiency was generally best if these reagents were contacted with replated hES cells ~48 h after the replating.

Transfection using Lipofectamine 2000™ was conducted as follows: The plasmid DNA (3-5 μg of pEGFP-C1, ClonTech cat. # 6084-1) was diluted in water to a final volume of 100 μl. In pilot experiments, 5 to 30 μL of Lipofectamine 2000™ (Gibco, cat # 11668-019) were diluted in Opti-MEM™ (Gibco, cat # 11-58-021) to a final volume of 100 μL. The DNA solution was then added slowly to the Lipofectamine2000™ solution and mixed gently. The mixture was incubated at room temperature for 20-30 min before being supplemented with 800 μl of OptiMEM™. Cells were washed with 3 mL of pre-warmed OptiMEM™ and incubated in 0.5-1 mL of the DNA/lipid mixture solution at 37° C. for 4 h, per well (9.6 cm$^2$). In some experiments, at 4 h the complex was removed before the addition of 4 mL of mEF-conditioned medium; in others sufficient mEF-conditioned medium was added to the wells to reach a final volume of 3.5 mL and the mixture was left on the cells overnight. In other experiments the DNA:lipid mixture was added to wells containing sufficient mEF-conditioned medium such that the final volume was 3.5 mL, and the cells were incubated in this mixture overnight.

Transfection using FuGENE™ was conducted as follows. Each well was transfected with 10 μg DNA using FuGENE™ 6 (Roche Diagnostics Corp.), at a ratio of 3:2 FuGENE™ reagent to DNA as described by the manufacturer's directions. OptiMEM™ serum-free medium was used in the transfections. In the "old protocol", 4 h after the addition of the FuGENE™-DNA complex, 2.5 mL of standard hES medium was added to each transfected well. In the revised protocol ("3:2 L"), transfected wells were not re-fed with standard hES medium. Twenty-four hours after transfection, GFP-expression was assessed by flow cytometry.

Forty-eight hours before transfection, hES cells were seeded onto 6 well plates that had been coated with gelatin and mEF feeder layers as described above. hES cells were transfected using FuGENE™ 6 (Roche) or Lipofectamine 2000™ (Gibco) according to the manufacturers' instructions.

Twenty-four hours after transfection, cells were assessed for GFP expression by inspection under a fluorescent microscope or flow cytometry. In the experiment shown in FIG. 1, three methods were compared: the standard Lipofectamine 2000™ protocol, the standard FuGENE™ protocol, and a variant FuGENE™ protocol in which the DNA/lipid mix was left on the cells overnight. The results demonstrated that while Lipofectamine 2000™ consistently yielded a higher percentage of GFP-expressing cells, the variant FuGENE™ protocol resulted in GFP-expressing cells with a higher mean fluorescence intensity.

Transient transductions using adenoviral vectors were conducted as follows. The vector Ad5CMV5-GFP (referred to here as Ad5GFP) contains the green fluorescent protein encoding region under control of the CMV promoter, and was purchased from Quantum Biotechnologies, cat # ADV0030. Seventy-two hours before transduction, hES cells were seeded onto 24 well plates that had been coated with gelatin and mEF feeder layers as described above. Before transduction, 3 wells of hES cells were detached with a solution of 0.05% trypsin/5mM EDTA (Sigma) at 37°, resuspended in 500 µL of standard mEF growth medium, and counted with a hemocytometer (the 75,000 mEF feeder cells were subtracted from each well) to establish the cell number before transfection. The adenovirus stock was thawed on ice immediately prior to use.

For infection with Ad5GFP, growth media was aspirated from the wells containing hES cells and replaced with 1 mL of hES medium plus 9 µL of Ad5 GFP stock (MOI of 40). Two hours later, the virus-containing medium was replaced with 1 mL of hES medium per well. Each transduced well was refed with 1 mL of fresh hES medium every 24 hours. GFP expression was assessed by flow cytometry. The results from a typical experiment indicated that expression was highest at 24 hr after transduction but persisted for at least 8 days at low levels (by the later time points, extensive differentiation had occurred due to overgrowth of the hES cells).

Figure 3:
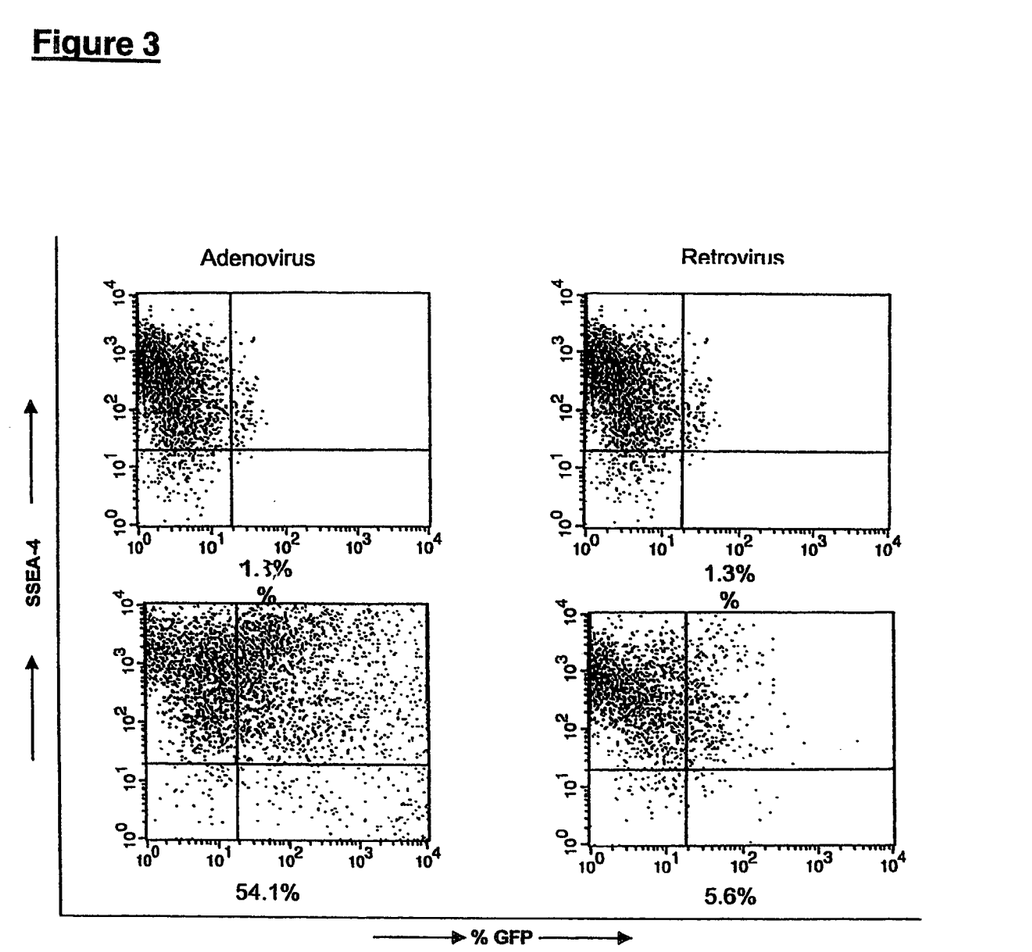
FIG. 3 is a FACS profile of transduced hES cells for GFP expression and SSEA-4, a marker of undifferentiated cells. hES cells were plated on feeder layers and infected 48 h later with either the adenoviral vector Ad5GFP or the retroviral vector GRN354, both of which include a GFP expression cassette. The cells were harvested, stained with an antibody against SSEA-4, and assessed for GFP expression by low cytometry. Upper panels show the background fluorescence and SSEA-4 positive staining in mock-infected cultures. Lower panels show the level of green fluorescence resulting from expression of the GFP.

FIG. 3 shows FACS analysis of hES cells plated on feeder layers and infected 48 h later with either the adenoviral vector Ad5GFP (MOI of 30) or the retroviral vector GRN354 (MOI of 40). After 24 h or 48 h respectively, the cells were harvested, stained with an antibody against the stem cell marker SSEA-4, and assessed for GFP expression by flow cytometry. Upper panels show the background fluorescence and SSEA-4 positive staining in mock-infected cultures. Lower panels show the level of green fluorescence resulting from expression of the GFP.

Example 4

Preparation of Immortalized Feeder Cells

Primary mouse embryonic fibroblasts (Robertson, supra) can be immortalized by genetically altering them to express human telomerase reverse transcriptase (hTERT). The fibroblasts (mEF) are infected with a retroviral construct pBABE puro hTERT, containing the hTERT coding sequence driven by the MOLV LTR and the puromycin-resistance gene driven by the SV40 early promoter. Isolates of primary mEFs are cultured in growth medium containing 10% fetal calf serum (HyClone), 2 mM glutamine (Gibco/BRL), and 90% high glucose DMEM (Gibco/BRL). mEFs are split every 3 days at a ratio of 1:2.

After 4 such splits, $5 \times 10^5$ mEFs are plated onto a 100 mM dish. On the next day, cells are infected by replacing the growth medium with a mixture containing 5 mL of retroviral stock ($1 \times 10^6$ pfu/mL) and 4 µg/mL polybrene, and incubating at 37° C. After 8 h, an additional 5 mL of the retrovirus/polybrene mixture is added and the cells are incubated at 37° C., On the next day, the retrovirus/polybrene mixture is removed and replaced with fresh growth medium. After 4 hr, the mEFs are removed from the plate with 0.5% trypsin/500 mM EDTA (Gibco/BRL) and replated into 2 T150 flasks in 25 mL growth medium/flask. On the next day, the medium is replaced with growth medium supplemented with 0.5 micrograms/mL puromycin.

Cells are split once a week at a ratio of 1:4 for 8 weeks and maintained in puromycin-containing medium. After 8 weeks, cells are trypsinized and replated at a density of 2,000 cells per 150 mm plate. Individual colonies are isolated with cloning cylinders 26 days later, expanded, and screened for telomerase activity.

Mouse Feeder Cell Line NH190

A permanent mouse cell line has been established that is suitable for conditioning medium for the culture of primate pluripotent stem (pPS) cells. The NHG190 line is a mouse embryonic fibroblast cell line immortalized with telomerase that is triple drug resistant, and expresses green fluorescent protein (GFP).

Two mouse strains were obtained from Jackson Laboratory (Bar Harbor, Me.) that have a transgene for resistance to the antibiotics neomycin or hygromycin. The C57BL6J TgN (pPGKneobpA)3Ems mice and C57BL6J-TgN (pPWL512hyg)1Ems mice from Jackson Labs were crossbred. Embryos that were both neomycin- and hygromycin-resistant were dissected at day 13.5 post conception according to standard protocols for preparing mouse embryonic fibroblasts (mEF) for feeder layers (E. J. Robertson, pp. 71-112 in *Teratocarcinoma and Embryonic Stem Cell Lines*, ed. E. J. Robertson, Oxford: IRL Press, 1987). The derived mEF cells were stored frozen.

The mEFs were thawed in growth medium containing 20% fetal calf serum (HyClone), 2 mM L-glutamine (Gibco/BRL), 80% DMEM (Gibco/BRL). The cells were expanded using 1:2 split ratios for 4 passages. Two flasks that had reached ~75% confluence were fed with fresh medium 4 h before electroporation. Cells were removed from the flasks with 0.5% trypsin/500 mM EDTA (Gibco/BRL), pelleted at 400×g for 5 min at room temperature, and resuspended in the growth medium at a concentration of $4 \times 10^6$ cells/mL.

The cell suspension was divided into two 500 µL aliquots and transferred to two 0.4 cm gap electroporation cuvettes (BioRad). One cuvette received 5 µg of the control plasmid (pBS212; puromycin-resistance gene driven by the SV40 early enhancer/promoter); the other received 5 µg of pGRN190, comprising the murine telomerase reverse transcriptase (mTERT) coding region driven by MPSV promoter plus puromycin resistance gene driven by the SV40 early enhancer/promoter. The cells and DNA were mixed by hand, and electroporated using a BioRad gene Pulser with a BioRad capacitance extender at a setting of 300V, 960 µF.

Each aliquot of cells was transferred to an individual 150 cm plate containing 25 mL of growth medium. The medium on the plates was exchanged on the following day, and on the next day, growth medium was replaced by growth medium plus 0.5 µg/mL puromycin. The medium on the plates was exchanged for fresh puromycin-containing medium every 48 hrs until 29 days after electroporation. At this time, large individual colonies of puromycin-resistant cells were evident in both the pBS212- and pGRN190-electroporated plates. Ten colonies from the control plate and 12 from the pGRN190-electroporated plate were isolated with cloning cylinders and each colony was transferred to 1 well of a 48-well plate (1 well per colony).

One week later, all surviving colonies that had expanded to reach confluence in the 48 well plate (three control colonies, 1 pGRN190-electroporated colony) were transferred individually to wells of a 24 well plate. Six days later, the only colony that had continued to expand was derived from the pGRN190-electroporated plate, and was subsequently designated NH190. The cells were maintained in growth medium plus 0.5 μg/mL puromycin. Analysis for telomerase activity by TRAP assay (Kim et al., Nucleic Acids Res. 25:2595, 1997) demonstrated that NH190 cells express functional telomerase activity.

To facilitate monitoring of the cells in mixed culture populations and in vivo, NH190 cells were further infected with a retroviral construct conferring expression of green fluorescent protein (GFP). The enhanced GFP sequence from plasmid pEGFP-1 is one of the Living Colors™ fluorescent protein vectors, available from ClonTech. It contains an enhanced GFP encoding region, with changes that alter restriction nuclease cleavage sites, and shift the excitation and emission wavelengths of the encoded protein. The EGFP-1 sequence was cloned into the vector pMSCV.neo, ClonTech cat # K1062-1. NH190 cells were transduced with the engineered vector, and GFP positive cells were separated by FACS sorting. The GFP expressing cell line was designated NHG190. These cells have been carried in culture for over 3 months.

Human Feeder Cell Line

A human embryonic fibroblast (hEF) like cell line was developed from the hES cell line designated H1. To form embryoid bodies, the hES cells were harvested after incubation with collagenase IV, and dissociated into small clusters in differentiation media and cultured in non-adherent cell culture plates to form aggregates in suspension. After 4 days, they were plated onto gelatin-coated plates for an additional 9 days. The cultures were incubated in 2 mg/mL Collagenase type II in PBS for 30 min at 37° C. The cells were harvested, dissociated, centrifuged, resuspended in differentiation medium, and plated in a 6-well plate. The proliferating cells were passaged in hEF medium (90% DMEM, 10% heat-inactivated FBS, 0.1 mM non-essential amino acids, and 2 mM L-glutamine), and fed every 2-3 days. After two passages, the cell population appeared homogeneous with morphological characteristics of fibroblasts. This hEF cell line was designated HEF1. Subpopulations were transduced with the retrovirus telomerase expression vector (pBABE-hTERT), or with vector control.

The growth curves of the hTERT-transduced HEF1 cells, and cells transduced with vector control were compared. Both lines doubled about once every 2 days, until the 38 day point, when the control cells stopped dividing (presumably because they had reached the Hayflick limit). The hTERT-transfected cells continued proliferating beyond the 60 day point (30 doublings) at a consistent growth rate.

Example 5

Genetic Alteration of hES Cells Maintained on the Drug-Resistant NHG190 Feeder Cell Line NHG190 cells described in Example 4 were cultured in DMEM (Gibco) plus 20% fetal bovine serum (HyClone) and 5 mM glutamine. Cells were split 1:10 every 3 days. Subconfluent cultures were detached with trypsin, suspended in 10 mL medium, and irradiated with a cumulative dose of 3500 rads with a Torrex 150D X-ray generator. Irradiated cells were pelleted at 400×g for 5 min and resuspended at $1.25 \times 10^5$ cells per mL in either NHG190 medium or standard hES medium.

hES cells were transfected by replating on a 6-well plate precoated with Matrigel® and NHG190 feeder cells. Forty-eight hours after seeding, the hES cells were transfected with 10 μg DNA per well using FuGENE™ 6 (Roche) according to manufacturer's protocol in OptiMEM™ serum-free medium. The DNA was a plasmid containing the PGK promoter driving $neo^r$. Four h later, 3 mL of NHG190-conditioned medium was added to each transfected well. Cells were re-fed daily with 3 mL conditioned medium. Forty-eight h after transfection, the cells were layered with NHG190 conditioned medium containing 200 μg/mL added geneticin (Sigma), which was replaced daily thereafter. After 3 days of selection, additional irradiated NHG190 feeder cells were added ($1.25 \times 10^5$ cells/well in hES medium). Twenty-four h later, the medium was again replaced with NHG190-conditioned medium containing 200 μg/mL geneticin, replaced daily.

Individual colonies were isolated and expanded through another round of selection. After a further 5 days, individual colonies were identified by microscope and marked on the outside of the dish. Medium was removed, and replaced with collagenase (~200 U/mL). Individual colonies were picked using a p20 pipet tip, and transferred to individual tubes containing 2 mL NHG190 conditioned medium (without geneticin). The suspension was triturated 5 times to disaggregate colonies, and the contents of each tube were transferred to a well of a 12-well plate coated with gelatin and irradiated NHG190 cells ($1.875 \times 10^5$ cells/well). Cells were fed 24 h later with 2 mL fresh conditioned medium. Two days after seeding, cells were layered with 2 mL conditioned medium containing 200 μg/mL geneticin, replaced daily for 5 days. As each well became 50-75% confluent, the cells were detached with collagenase, transferred to 6 mL conditioned medium, and triturated 10-12 times. 3 mL cell suspension was added to each of 2 wells of a 6-well plated coated with gelatin and irradiated NHG190 cells ($3.75 \times 10^5$ cells/well); the cells were refed with 3 mL conditioned medium at 24 h. The cells were then selected for 5 days using 3 mL conditioned medium containing geneticin, and split 1:6 as before.

Stable transduction using retrovirus was conducted as follows. Retroviral vector designated GRN354 was constructed at Geron Corp. using PMSCVneo vector purchased from ClonTech (cat # K1062-1). The eGFP encoding region was inserted downstream from the MSCV LTR. The LTR drives expression of GFP, and the vector also contains the $neo^r$ gene driven by the murine PGK promoter. Plates were coated with 0.5% gelatin and NHG190 feeder cells ($7.5 \times 10^4$ in 1 mL NHG190 medium for 24 well plates; $3.75 \times 10^5$ in 3 mL medium for 6 well plates). The hES line H7 was seeded onto a 24 well prepared plate in hES medium (1 mL/well). Forty-eight h later, 3 wells of hES cells were detached using 0.05% trypsin/5 mM EDTA (Sigma) at 37° C., resuspended in 500 μL NHG190 medium, and counted. Stock of retrovirus construct pGRN354 was thawed on ice immediately prior to use. Growth medium was aspirated from the wells and replaced with 400 μL hES medium plus 8 μL retrovirus (MOI of 10) and 4 μL of 8 mg/mL polybrene solution (Sigma). Two h later, 800 μL hES medium were added per well. Each transduced well was refed with 1 mL fresh hES medium every 24 h.

Four days after transduction, medium was replaced with 1 mL hES medium containing 200 μg/mL geneticin. After 3 days of geneticin selection, the cells were detached with collagenase, triturated, resuspended in 3 mL hES medium, reseeded into one well of a 6-well plate coated with gelatin and NHG190 feeders, and refed with hES medium after 24 h.

The medium was then again replaced with hES medium containing geneticin and refed every 24 h. Undifferentiated colonies survived the selection, and have been maintained for over 3 months. FACS analysis showed that 50-65% of the selected cells express GFP, albeit at low levels. The karyotype of the cells was normal.

The cells were then transferred to suspension culture to form embryoid bodies, allowed to differentiate for 4 days, and then plated in 20% FBS medium for 1 week. After extensive differentiation occurred, the cultures were fixed in 4% paraformaldehyde and prepared for fluorescence microscopy. Many of the differentiated cells expressed higher levels of GFP than the undifferentiated transfected hES cell line, consistent with differential activation of the MESV-LTR in different cell types.

Example 6

Transfection of hES Cells in Feeder-Free Culture hES cells maintained in feeder-free culture on laminin in conditioned medium were genetically modified by transfecting with a plasmid carrying green fluorescent protein (GFP) driven by the CMV promoter.

mEF conditioned medium was prepared as described earlier. mEFs were irradiated and seeded at about $5.7 \times 10^4$ cells $cm^{-2}$. After at least 16 hours the medium was exchanged with hES medium including 4 ng/mL added hbFGF. Conditioned medium was collected daily for feeding of hES cultures. Before addition to the hES cultures, this medium was supplemented with an additional 4 ng/mL of hbFGF. Where needed for selection of stable transfectants, the mEF-conditioned medium was supplemented with 200 µg/mL geneticin (Sigma cat. # G5013).

H9 hES cells maintained on mEF feeder layers were harvested from cultures by incubation with ~200 units/mL collagenase IV at 37° C. for 10 min. Cells were dissociated and resuspended in regular hES medium or mEF-conditioned medium. Cells in the regular medium were then re-seeded onto mEF feeder layers and cells in the mEF-conditioned medium were plated onto Matrigel[ or laminin. Seeding density for all cultures was approximately $4 \times 10^4$ cells/cm$^2$. Cells on feeder layers were maintained in regular medium while cells on matrices were maintained in mEF-conditioned medium for 1 or 2 days before the transfection. Conditioned medium was replaced every 24 h.

hES cell cultures were transfected with Lipofectamine 2000™ as described above. FACS analysis of GFP expression was conducted as follows. hES cells were harvested using 0.5 mM EDTA in PBS and resuspended at approximately $1 \times 10^6$ cells/test. Cells were washed in a solution containing PBS plus 2% FBS, 0.1% sodium azide, and 2 mM EDTA. SSEA-4 staining was performed in the same buffer using antibody obtained from the Developmental Studies Hybridoma Bank (University of Iowa, Iowa City) at 1:15 dilution. Isotype matched controls were obtained from Sigma, (St. Louis Mo., USA). Cells were incubated with antibodies in a final volume of 100 µl for 30 min at 4° C., washed and incubated with rat anti-mouse K chain antibodies conjugated with PE (Becton Dickinson, San Jose, Calif.) at 4° C. for 30 min. Samples were washed as before and analyzed for GFP and SSEA-4 expression on FACScalibur™ flow cytometer (Becton Dickinson, San Jose, Calif.) using CellQuest™ software.

hES cells of the H9 line maintained on laminin in mEF-conditioned medium were transfected with a plasmid carrying GFP driven by the CMV promoter at 24 or 48 h after plating. Initial experiments used a mixture of 5 µg of plasmid and 12 µL of Lipofectamine 2000™. Cells received 1 mL of DNA/lipid complex and were incubated for 4 h at 37° before the addition of 3 mL of mEF-conditioned medium, and then monitored for GFP expression 24 h after transfection.

Figure 4:
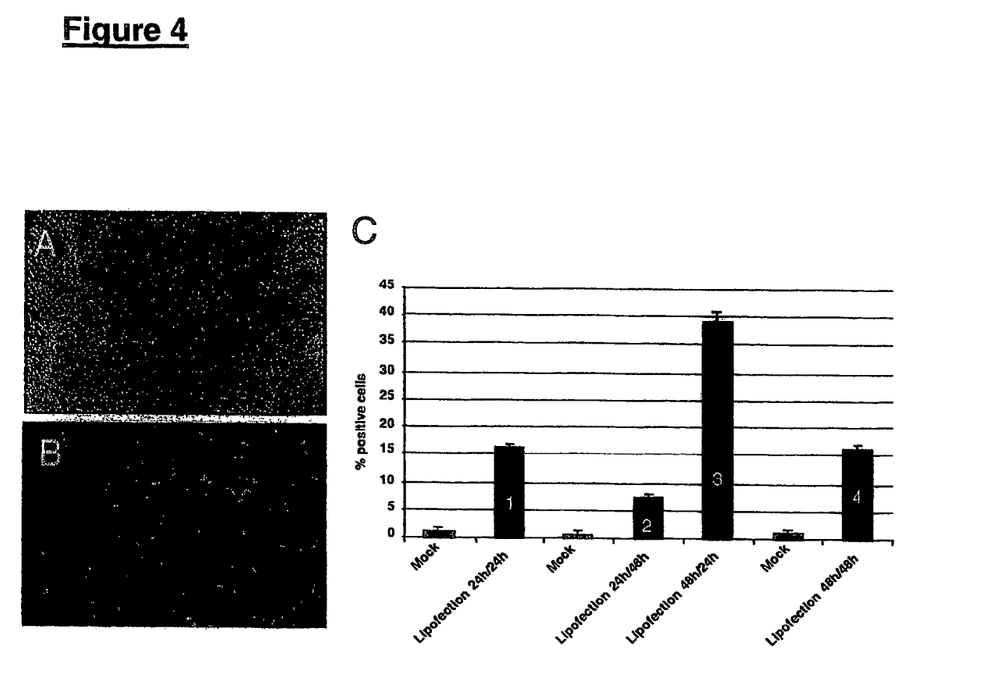
FIG. 4 shows the results of an experiment in which hES were genetically altered in feeder-free culture by lipofection. Panel A is a half tone of a light micrograph showing morphology of hES cells on laminin after they have been transfected for GFP expression. Panel B is a half tone of a fluorescence micrograph showing GFP expression in the same colony. Panel C is a bar graph showing percentage of cells expressing GFP under various conditions.

FIG. 4 shows the results of this experiment. Panel A: morphology of H9 cells maintained on laminin. Panel B: GFP-positive cells observed in the same colony shown in A. Panel C: FACS analysis of % GFP-positive cells in SSEA-4 high population(undifferentiated cells). Cells were transfected 24 (bar 1 and 2) or 48 h (bar 3 and 4) after the seeding and analyzed 24 (bar 1 and 3) or 48 h (bar 2 and 4) after the transfection. Bright green cells were observed in compact areas of undifferentiated ES colonies on laminin 24 h after transfection (Panels A & B). Transfection at 48 h after initial seeding gave the highest efficiency: 38% of the cells were GFP-positive as determined by FACS analysis 24 h after the transfection (Panel C).

The next experiment compared the transfection efficiency of H9 cells maintained on Matrigel® or laminin-coated plates in mEF-conditioned medium with cells maintained on mEF feeders. Cells on feeder layers maintained in regular medium were used as a control. Morphological differences between cells on feeders and cells off feeders were observed 1 or 2 days after seeding. Colonies on feeders were more compact than cells maintained off feeder layers; individual hES cells in feeder-free cultures were less compact and flatter. There was no significant difference in cell or colony morphology between cells on laminin and cells on Matrigel. These cells were transfected with a plasmid expressing GFP driven by the CMV promoter 2 days after seeding. Twenty-four hours after the transfection, cells were examined for GFP expression under a fluorescence microscope.

Figure 5A:
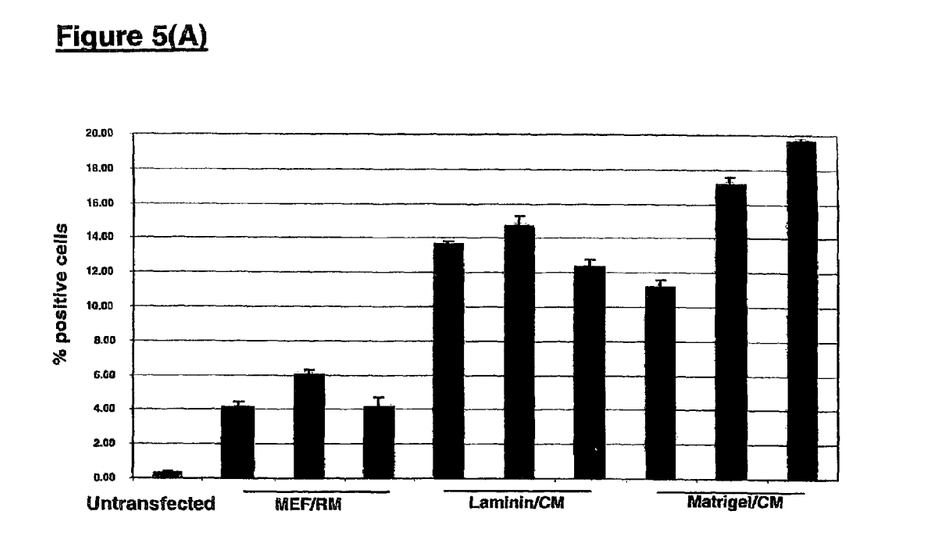
FIG. 5 is a bar graph showing the percentage of GFP-positive cells in SSEA-4 positive cell population (undifferentiated ES cells). Panel A: Bright green cells were observed in undifferentiated hES colonies of feeder-free cultures. In contrast, very few green cells were found in hES cell colonies grown on feeders. FACS analysis showed that 16% of cells on Matrigel® and 14% of cells on laminin were GFP positive in the SSEA-4 positive (undifferentiated) cell population, while only 5% of cells on feeders were positive, showing that transfection efficiency is significantly increased by using feeder-free conditions. Panel B shows transfection efficiencies of a GFP reporter plasmid using different conditions of Lipofectamine 2000™ (L) or FuGENE™ (F).

The cells were maintained on mEF feeders in regular medium (mEF/RM), on laminin in medium conditioned by mEF (Laminin/CM) or on Matrigel® in the conditioned medium (Matrigel/CM). As shown in FIG. 5(A), bright green cells were observed in undifferentiated hES colonies of feeder-free cultures. In contrast, very few green cells were found in colonies on feeders. FACS analysis showed that 16% of cells on Matrigel® and 14% of cells on laminin were GFP positive in SSEA-4 high population while only 5% of cells on feeders were positive. These results indicate that transfection efficiency is significantly increased by using feeder-free conditions.

The next experiments evaluated the effects of 1) the ratio of DNA:lipid; 2) adding the DNA/lipid complex to cells 4 h prior to the addition of mEF-conditioned medium vs. addition of the complex to cells in the presence of mEF-conditioned medium; and 3) use of Lipofectamine 2000™ vs. FuGENE™.

Transfection using Lipofectamine2000™ is described above. Transfection with FuGENE™ was conducted as follows. The plasmid DNA (5-10 µg of pEGFP-C1, ClonTech cat. # 6084-1) was diluted in wate to a final volume of 100 µl. In pilot experiments, 5-30 µL of FuGENE™ were added to sufficient OptiMEM™ to achieve a final volume of 100 µL. The DNA solution was then added slowly to the FuGENE™ solution and mixed gently. The mixture was incubated at room temperature for 30 min before being supplemented with 800 µl of OptiMEM™. Cells were washed with 3 mL of pre-warmed OptiMEM™ and incubated in 1 mL of the DNA/lipid mixture solution at 37° C. for 4 h. In some experiments, at 4 h the wells received an additional 2 mL of mEF-conditioned medium; in others the DNA/lipid mixture was added to wells containing 2 mL of mEF-conditioned medium and the cells were incubated in this mixture overnight.

Figure 5B:
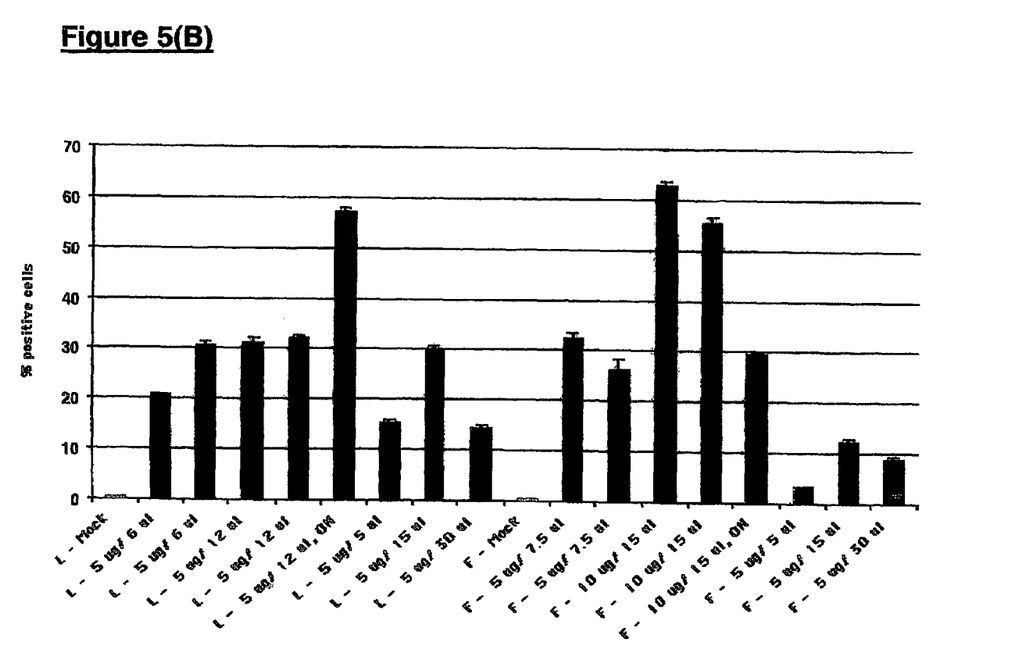

The results are shown in FIG. 5(B). Highest efficiencies were obtained under the following conditions: Bar 1=a mixture of 5 µg plasmid plus 12 µl of Lipofectamine 2000™, adding 1 mL of the DNA/lipid mixture to wells containing 2.5 mL of mEF-conditioned medium and incubating the cells in this mixture overnight. Bars 2 & 3=a mixture of 10 µg plasmid plus 15 µl of FuGENE™ and incubating the cells in 1 mL of the DNA/lipid mixture for 4 h before adding 2.5 mL of mEF-conditioned medium. L=Lipofectamine2000™; F=FuGENE™.

In another series of experiments, hES cells were transfected after being detached from the matrix in feeder-free culture using a solution of 0.5 mM EDTA in sterile PBS (instead of collagenase). Cells were incubated for 5 min at 37° C., until individual cells began to round up. The EDTA solution was then removed, and ~1 mL of conditioned medium was pipetted into the well, detaching the cells. The resultant clusters were then replated in a new feeder-free culture at a split ratio of 1:3 or 1:6. Under these conditions, the highest transient transfection efficiency was achieved when the cells were lipofected 24 h after seeding.

To investigate whether the feeder-free hES cells undergo stable genetic modification, H1 hES cells maintained on Matrigel® were cotransfected with a mixture of 7.5 µg plasmid carrying β-galactosidase driven by the EF1a promoter, and 2.5 µg of plasmid carrying the PGK promoter driving the neophosphotransferase gene. The cells were transfected 48 h after plating them on Matrigel® in mEF-conditioned medium. 10 µg of plasmid plus 15 µl of FuGENE™ were incubated with the cells in 1 mL for 4 h before adding 2.5 mL of mEF-conditioned medium. After 48 h, medium was exchanged for mEF-conditioned medium supplemented with 200 µg/mL geneticin. Cultures were maintained in this geneticin-containing medium with daily medium exchange for over 21 days. All mock-transfected cultures (i.e., those that received FuGENE™ mixed with water rather than plasmid) died within 48-72 h. Drug resistant colonies arose in the wells transfected with both FuGENE™ and plasmid at a frequency of about 1 in to $10^5$ originally transfected cells. The colonies were maintained in geneticin-containing mEF-conditioned medium and expanded.

The compositions and procedures provided in the description can be effectively modified by those skilled in the art without departing from the spirit of the invention embodied in the claims that follow.

The invention claimed is:

1. A method of obtaining genetically modified human embryonic stem ("hES") cells, comprising:
   a) providing an in vitro culture of hES cells essentially free of feeder cells, wherein the culture is maintained in a culture environment that contains an extracellular matrix and fibroblast-conditioned medium;
   b) transfecting the hES cells with a polynucleotide; and
   c) maintaining the transfected hES cells in a culture environment that contains an extracellular matrix and fibroblast-conditioned medium;

thereby obtaining genetically modified hES cells.

2. The method of claim 1, further comprising preferentially selecting the genetically modified hES cells.

3. The method of claim 1, wherein the polynucleotide comprises a protein encoding region operably linked to a promoter that promotes transcription of the encoding region in an undifferentiated hES cell.

4. The method of claim 3, wherein the polynucleotide is contained within a vector selected from the group consisting of an adenoviral vector, a retroviral vector, a lentiviral vector, and a DNA plasmid complexed with a positively charged lipid.

* * * * *